(12) United States Patent
Samoylova et al.

(10) Patent No.: US 7,642,063 B2
(45) Date of Patent: *Jan. 5, 2010

(54) METHODS FOR TARGETING AND KILLING GLIOMA CELLS

(75) Inventors: Tatiana I. Samoylova, Auburn, AL (US); Henry J. Baker, Auburn, AL (US); Nancy R. Cox, Auburn, AL (US); Ludmila P. Globa, Auburn, AL (US); Nancy E. Morrison, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/132,879

(22) Filed: May 19, 2005

(65) Prior Publication Data

US 2005/0260133 A1    Nov. 24, 2005

Related U.S. Application Data

(60) Provisional application No. 60/572,511, filed on May 19, 2004.

(51) Int. Cl.
*A61K 38/17* (2006.01)
*A61K 51/00* (2006.01)
*G01N 33/574* (2006.01)

(52) U.S. Cl. .................. 435/7.23; 424/1.49; 514/2
(58) Field of Classification Search .............. 435/7.23
See application file for complete search history.

(56) References Cited

U.S. PATENT DOCUMENTS 7,094,868 B2    8/2006    Samoylova et al.
2003/0216322 A1    11/2003    Samoylova et al.

OTHER PUBLICATIONS

Petrenko et al. (Prot. Eng. 9(9):797-801 (1996)).*
Yip et al. (Curr. Pharm. Biotechnol. 3:29-43 (2002)).*
Nilsson et al. (Adv. Drug Deliv. Rev. 43:165-196 (2000)).*
Sathornsumetee et al. (Cancer 110(1):13-24 (2007)).*
Mamelak et al. (Expert. Opin. Drug Deliv. 4(2):175-186 (2007)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Allen, "Ligand-Targeted Therapeutics In Anticancer Therapy," Nature Reviews/Cancer, vol. 2, 750-763 (Oct. 2002).
Brown, "New Approaches for Cell-Specific Targeting: Identification of Cell-Selective Peptides from Combinatorial Libraries," Current Opinion in Chemical Biology, 4:16-21 (2000).
Chen et al, "RGD-Tachyplesin Inhibits Tumor Growth," Cancer Research 61:2434-2438 (2001)A.
Ellerby et al, "Anti-Cancer Activity of Targeted Pro-Apoptotic Peptides," Nature Medicine 5:1032-1038 (1999).
Landon et al, "Combinatorial Discovery of Tumor Targeting Peptides Using Phage Display," Journal of Cellular Biochemistry, p. 90:509-517 (2003).
Samoylova et al, "Phage Probes for Malignant Glial Cells," Molecular Cancer Therapeutics, pp. 1129-1137 (2003).
Aina et al, "Therapeutic Cancer Targeting Peptides," Biopolymers 66:184-199 (2002).
Brogden et al, "Antimicrobial Peptides in Animals and Their Role in Host Defenses," International Journal of Antimicrobial Agents 22:465-478 (2003).
Kelly and Jones, "Isolation of a Colon Tumor Specific Binding Peptide Using Phage Display Selection," Neoplasia 5:437-444 (2003).
Papo et al, "A Novel Lytic Peptide Composed of DL-Amino Acids Selectively Kills Cancer Cells in Culture and In Mice," Journal of Biological Chemistry 278:21018-21023 (2003).
Papo et al, "New Lytic Peptides Based on the D,L-amphipathic Helix Motif Preferentially Kill Tumor Cells Compared to Normal Cells," Biochemistry 42:9346-9354 (2003).
Samoylova et al., "Molecular Markers of Glial Tumors: Current Targeting Strategies," Current Medicinal Chemistry, 10:831-843 (2003).

* cited by examiner

*Primary Examiner*—Lynn Bristol
(74) *Attorney, Agent, or Firm*—Andrus, Sceales, Starke & Sawall, LLP

(57) ABSTRACT

A diagnostic technique for matching anti-cancer peptide drugs to the molecular profiles of individual cancer tumors, and a method using the technique for a patient-specific treatment of tumors in mammals. This strategy matches anti-cancer peptide drugs to the molecular profiles of individual tumors, and includes the development of two banks, both of which use the same targeting peptides. Targeting peptides are identified using biopsies or other tissue materials from multiple cancer patients and placed into two banks. For a bank of probes, targeting peptides are linked to a label such as a fluorescent or a radioisotope. For a bank of drugs, targeting peptides are linked to a cytotoxic peptide to form a "targeting peptide drug". Peptide probes are used to establish molecular profiles of individual tumors. Based on these molecular profiles, a patient-specific combination of targeting drugs from the bank of peptide drugs is prepared and the patient is treated. Any currently used cytotoxic agent that can be linked to targeting peptides may be used in place of cytotoxic peptides.

8 Claims, 6 Drawing Sheets

| FAMILY 1 | FAMILY 2 | FAMILY 3 |
|---|---|---|
| VDLPEHGK(9)* | DTTKTSAG(1) | ELRGDSLP(10) |
| VGLPEHTQ(5) | DSTKSGNM(1) | EVRGDSLP(2) |
| VGLPEHSA(4) | DSTKIGTS(1) | ESRGDSYA(2) |
| VDLPTHSS(7) | DSTKASDA(1) | |
| VDLPEHRQ(1) | DLTKSTAP(9) | |
| VDLPTHQS(1) | DYDMTKNT(1) | |

* NUMBERS OF IDENTICAL PHAGE COPIES

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Cys Asn Gly Arg Cys
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Ala Cys Asp Cys Arg Gly Asp Cys Phe Cys
1               5                   10

<210> SEQ ID NO 3
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 3

Asp Ser Thr Lys Ser Gly Asn Met
1               5

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Lys Leu Ala Lys Leu Ala Lys Lys Leu Ala Lys Leu Ala Lys
1               5                   10

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Asp Ser Thr Lys Gly Gly Lys Leu Ala Lys Leu Ala Lys Lys Leu Ala
1               5                   10                  15

Lys Leu Ala Lys
            20
```

METHODS FOR TARGETING AND KILLING GLIOMA CELLS

CROSS REFERENCE TO RELATED APPLICATION

The present application is based on and claims priority to U.S. Provisional Patent Application No. 60/572,511 filed May 19, 2004.

FIELD OF THE INVENTION

This invention relates to anti-cancer pharmaceutical drugs, and more particularly to a diagnostic technique for matching anti-cancer peptide drugs to the molecular profiles of individual cancer tumors, and to a method of using the technique for patient-specific treatment of such tumors in humans and animals.

BACKGROUND OF THE INVENTION

Cancer is a complex heterogeneous disease with molecular, morphological and clinical differences that exist both between and within tumors. While histopathologic features of tumor cell morphology, invasiveness and metastasis remain the "gold standard" for diagnosis and staging of cancers, molecular profiles of neoplastic cells based on DNA, mRNA, and/or protein alterations are rapidly being developed and utilized not only to augment diagnosis, but to provide new therapeutic measures. Of these profiles, the pattern of protein expression based on cell surface markers is the most functional, holding the potential to offer direct correlations between cancer cell "portraits" and therapeutic responses to anti-cancer drugs.

Several strategies have been implemented to date for identification of distinctive protein profiles for a given cancer. For example, separation of proteins on two-dimensional gels has been used widely for protein expression analysis in research laboratories for many years. However, such analyses are unlikely to be used routinely in a clinical setting due to their complexity and the absence of 2-D protein databases of different tumor types. A peptide microarray method was proposed recently by Aina et al, "Therapeutic Cancer Targeting Peptides," Biopolymers 66:184-199 (2002), for identification of cell surface binding profiles of cancer cells. With this technique, cell-specific peptides isolated by selection from a one bead-one compound (OBOC) combinatorial library were linked to a polystyrene slide in a microarray format and used to detect a binding profile of human T-lymphoma cells. While the method seems promising for profiling cancer cells derived from individual cancer specimens, the diversity of OBOC libraries is relatively low and could be a limiting factor for their broad applications.

Invented less than 20 years ago, phage display technology is now well known in the art, and is used to produce valuable targeting peptides to a variety of cell types, both in vitro and in vivo. Phage display libraries are heterogeneous mixtures of billions of phage clones. Within a library, each clone carries a different foreign DNA insert and, therefore, displays the corresponding unique peptide on its surface. Different types of phage display libraries exist, depending upon the size of the insert, gene location of insert (resulting in pIII or pVIII phage display), structure of the displayed foreign peptide, and number of copies expressed on the surface of the phage. Importantly, the diverse and complex nature of random peptide libraries have the capacity to provide unique peptide sequences for any target receptor molecules, including those that are well-described and those that are previously undetected. This feature is especially important in ligand development for anti-cancer strategies, since tumors are composed of heterogenic cells that express different levels of cell-specific markers in the majority of patients.

Discovered in early 1980's, antimicrobial lytic peptides have been and continue to be studied extensively as a source of new anti-infective and recently anti-cancer agents. Antimicrobial peptides are a large group of gene-encoded molecules produced by almost all eukaryotic organisms including plants, insects, amphibians, and mammals. They are activated shortly after infection as part of the innate immunity of these species and rapidly destroy a broad range of invading microorganisms. In mammals, the major families of antimicrobial lytic peptides are the defensins and the cathelicidins that provide a first line of defense against pathogens. They are found in many tissues exposed to microbes such as mucosal epithelial surfaces and skin, as well as in professional phagocytes.

At present, thousands of native and de novo designed antimicrobial peptides are known. For example, an updated list of antimicrobial peptides from domesticated animals can be found in Brogden et al, "Antimicrobial Peptides in Animals and Their Role in Host Defences," International Journal of Antimicrobial Agents 22:465-478 (2003). Sequences of over 750 eukaryotic antimicrobial peptides have been reported and can be obtained from protein databases. Many of antimicrobial peptides are relatively short (15-40 amino acids), cationic (carry a positive net charge), alpha-helix-forming, amphipathic (with hydrophobic residues distributed on one side of the helical axis and cationic residues on the other) molecules. Because of these properties, they attack similar targets, which are the bacteria phospholipid membranes with highly negatively charged outer surfaces determined by high content of anionic phospholipids. These peptides perform their antimicrobial function using a common general mechanism. The hydrophilic, cationic part of the peptide is proposed to initiate electrostatic interaction with the negatively charged components of the bacterial membrane. The hydrophobic portion of the peptide then is inserted into and permeates the membrane causing membrane disintegration.

Selective toxicity of microbial peptides is thought to be due to the composition and structure of bacterial membrane, which maintain large transmembrane potentials and has a higher content of anionic phospholipids on its outer leaflet. In contrast, mammalian cell membrane is composed of zwitterionic (neutral) phospholipids and cholesterol that prevent interaction with the peptides and help to avoid host tissue damage. Some bactericidal peptides were found to be cytotoxic for mammalian cancer cells, Papo et al, "New Lytic Peptides Based on the D,L-amphipathic Helix Motif Preferentially Kill Tumor Cells Compared to Normal Cells," Biochemistry 42:9346-9354 (2003). While the mechanism of selectivity is not quite clear, it is believed that it can be partially explained by the differences in normal and cancer cell membrane composition. Similar to bacteria, cell membranes of tumor cells contain negatively charged phospholipids (3-9%). Interestingly, eukaryotic mitochondrial membrane is very similar to prokaryotic cytoplasmic membrane and can be a target for antimicrobial peptides as well.

In spite of the fact that some native cationic antimicrobial lytic peptides are more toxic to cancer cells than to normal mammalian cells, there are several limitations that prevent their application in cancer therapy. The use of native all L-amino acid antimicrobial peptides in vivo is limited in part because of enzymatic degradation and binding to components in serum. Additionally, they possess lytic activity toward blood cells. As a solution, Papo et al, "A Novel Lytic Peptide Composed of DL-Amino Acids Selectively Kills Cancer Cells in Culture and In Mice," Journal of Biological Chemistry 278:21018-21023 (2003) proposed de novo designed diastereomeric peptides (composed of both L- and D-amino acids). These peptides were derived from potent lytic peptides by replacing a few L-amino acids with their D-enantiomers. The resulting diastereomeric peptides lost their cytotoxic effect against normal mammalian cells, but preserved both their antibacterial activity and their ability to increase the permeability of negatively charged phospholipid membranes, including cytoplasmic membranes of cancer cells. The authors found that the selective activity of a 15-mer diastereomeric peptide toward cancer cells is a consequence of selective binding, mainly governed by electrostatic interactions between this cationic peptide and anionic phospholipids of cancer membranes. A short time after binding about 10 min), the cells died as a result of acute injury characterized by swelling and bursting, suggesting necrosis. ATR-FTIR studies showed that the peptide initially binds onto the surface and then is inserted into the membrane, destabilizing the membrane structure. At the same time, LD-amino acid peptides are not lytic toward normal mammalian cells.

To produce potent peptides with specific anti-cancer activity, several research groups constructed peptide molecules with two domains. One of the domains is a cell-targeting peptide, which is designed to guide the whole molecule to the target (tumor) cell, allowing cell-specific receptor-mediated internalization. The second domain is a lytic peptide which, after internalization, is able to destroy mitochondrial membrane and cause cell apoptosis. The whole peptide molecules are short, consist of 20-25 amino acids, and can be synthesized chemically with ease. Chen et al, "RGD-Tachyplesin Inhibits Tumor Growth," Cancer Research 61:2434-2438 (2001), examined a preparation of tachyplesin (17 amino acid antimicrobial peptide present in leukocytes of the horseshoe crab) that was linked to RGD peptide. RGD peptide is known to bind to integrins and thereby can facilitate internalization of tachyplesin. They found that this synthetic peptide with RGD-tachyplesin sequence could inhibit the proliferation of TSU prostate cancer cells and B16 melanoma cells in a dose-dependent manner in vitro and reduce tumor growth in vivo.

Ellerby et at, "Anti-Cancer Activity of Targeted Pro-Apoptotic Peptides," Nat. Med. 5:1032-1038 (1999), conjugated a short (14 amino acids) cationic lytic peptide with tumor-homing domain, either CNGRC (SEQ ID NO:1) or ACDCRGDCFC (SEQ ID NO:2). It was shown that the resulting peptides with dual function exhibited antitumor activity through their ability to target tumor cells and trigger apoptosis via disruption of mitochondrial membranes. Sequences of the tumor cell-targeting peptides used in this study were identified from screening of phage display libraries. Using phage display, Kelly and Jones, "Isolation of a Colon Tumor Specific Binding Peptide Using Phage Display Selection," Neoplasia 5:437-444 (2003), identified peptides that recognize colon carcinoma cells. One of the peptides was coupled to the mitochondrial toxin (the same as in Ellerby et al, "Anti-Cancer Activity of Targeted Pro-Apoptotic Peptides," Nature Medicine 5:1032-1038 (1999)) and added to HT29 colon carcinoma cells. As determined by MTT assay, HT29 cell viability after incubation with the peptide decreased in a concentration dependent manner.

SUMMARY OF THE INVENTION

A diagnostic technique for matching anti-cancer peptide drugs to the molecular profiles of individual cancer tumors, and a method of using the technique for patient-specific treatment of tumors in humans and animals is provided. Targeting peptide probes which are specific and selective for tumor cells are obtained, preferably using phage display technology, and placed into a bank or collection of such probes. The phage probes bearing targeting peptides are used to profile tumors at the molecular level. "Personalized" anti-cancer therapeutic peptides are then developed for each patient based on the probes that bind to the cancerous tumor cells. The therapeutic peptides are also selected from a bank or collection of such peptide drugs, and have two components: 1) the same targeting peptide itself which is identified via molecular profiling of the individual tumor and 2) a lytic peptide or other cytotoxic agent linked to the targeting peptide with proven cytotoxicity against a broad range of cancers. The therapeutic peptides or peptide drugs are rapidly and efficiently produced by chemical peptide synthesis for each patient.

One example of the novel anti-cancer strategy described herein is as a diagnostic technique for designing anti-cancer drugs. Such a technique may comprise the steps of:

(a) obtaining a sample of cancer cells;

(b) mixing the cancer cells with a bank of targeting probes, each targeting probe comprising a targeting peptide linked to a label;

(c) identifying one or more targeting probe that binds to the cancer cells;

(d) correlating the one or more targeting probe with a bank of peptide drugs, each peptide drug in said bank of drugs comprised of said targeting peptide linked to a cytotoxin;

(e) exposing the cancer cells to said one or more peptide drugs to induce a cytotoxic effect on said cancer cells; and (f) quantifying the cytotoxic effect on said cancer cells.

Another example of the novel anti-cancer strategy described herein is as a method of treating a cancerous tumor in mammals, comprising the steps of (a) obtaining a sample of cancer cells;

(b) mixing the cancer cells with a bank of targeting probes, each targeting probe comprising a targeting peptide linked to a label;

(c) identifying one or more targeting probe that binds to the cancer cells;

(d) correlating the one or more targeting probe with a bank of peptide drugs, each peptide drug in said bank of drugs comprised of said targeting peptide linked to a cytotoxin; and (e) administering the said one or more peptide drugs to a patient having a cancerous tumor to expose the cancerous tumor to said one or more peptide drugs and induce a cytotoxic effect thereto.

The above method for the development of "personalized" (patient-specific) drugs for the treatment of heterogenic tumors in man and animals includes the development of banks of peptide probes and peptide drugs. These banks are obtained by:

(1) collection of tumor sample (surgical specimen, biopsy, blood, etc.) from a patient;

(2) identification of targeting peptides which are specific and selective for this tumor using phage display technology and placing a sample of such targeting peptide in the peptide probe bank;

(3) synthesis of "personalized" anti-cancer therapeutic peptides each of which will be composed of two components—the targeting peptide which will perform tumor cell-specific delivery function and a cytotoxic peptide (or any other cytotoxic agent) which will perform tumor cell killing function, and placing a sample of such targeting drug in the peptide drug bank.

The method additionally encompasses the identification and characterization of phage probes bearing targeting peptides for multiple human tumor cell lines and primary cultures using phage display technology. Multiple phage display peptide libraries are screened with cell lines, primary tumor cell cultures, tissue sections, etc. to select and enrich for specific, high affinity phage probes for the tumor cells. Normal primary cell cultures are used in selection procedures to remove those phage which bind to cell surface markers common to cells of tumor origin.

The method additionally provides for the evaluation of patient-to-patient heterogeneity within human or animal tumors using phage probes bearing targeting peptides. To detect cell surface molecular differences between tumors from different patients, phage bearing targeting peptides are labeled (for example, with fluorescent dyes) and probed on tumor samples such as tissue sections, cell suspensions, tissue homogenates, etc. Different phage probes are labeled with different fluorescent dyes or other detection labels, thus a molecular profile of cell surface binding molecules for each patient is established and presented in relative numbers (%) that correspond to the intensity of each dye bound to the tumor sample. This technique is very similar to immunohistochemical staining but utilizes labeled phage probes rather than antibodies.

Phage provide several advantages as probes for cell surface markers: 1) phage probes can be developed for unknown, non-antigenic cell surface markers; 2) phage display libraries are readily available from commercial and private sources and are very diverse ($10^9$-$10^{10}$ variants per library); 3) propagation of phage in bacterial cultures is well standardized and inexpensive compared to antibody production in animals or cell cultures; and 4) phage preparations are stable without loss of titer for many years when stored at standard conditions. Probes designed using this approach may be applied instead of antibodies (that are expensive and can be developed only if the antigen is known and available) to profile individual tumor specimens, such as biopsies and tissue sections. Based on the cancer profile, a combination of anti-cancer drugs is designed to increase therapeutic effectiveness and reduce toxicity.

The method further provides for the design and testing of anti-tumor peptides with both targeting and killing abilities based on individual profiles of primary tumor samples. Peptides are designed which combine killing properties of lytic peptides with targeting abilities of cell-specific peptides. These peptides are synthesized using current peptide synthetic strategies. Cytotoxicity of these synthetic peptides with dual mode of action can be evaluated by MTT assay. Lytic effect of the peptides on cancer cells may be observed by dark-field microscopy.

The method further embodies (1) the binding and specificity of lytic peptides (tumor-killing peptides) which is increased via targeting peptides; (2) the selectivity of the therapeutic peptide is increased while the side effects of the drug is decreased; (3) the designed peptide will target both the cell membrane and mitochondrial membranes of cancer cells.

BRIEF DESCRIPTION OF THE DRAWINGS

The drawings illustrate the best mode presently contemplated of carrying out the invention.

In the drawings:

FIG. 4(*b*) is a graph of the binding ability of glioma-specific DSTKSGNM phage probe for glioma cancer cells versus other different cell types, including astrocytes, myoblasts, hepatocytes and fibroblasts;

FIG. 5(*b*) is a graph of peptide concentrations versus absorbance illustrating the cytotoxic effect of the peptide drug (cytotoxic peptide) on glioma cancer cells and normal astrocyte cells.

DETAILED DESCRIPTION OF THE INVENTION

Figure 1:
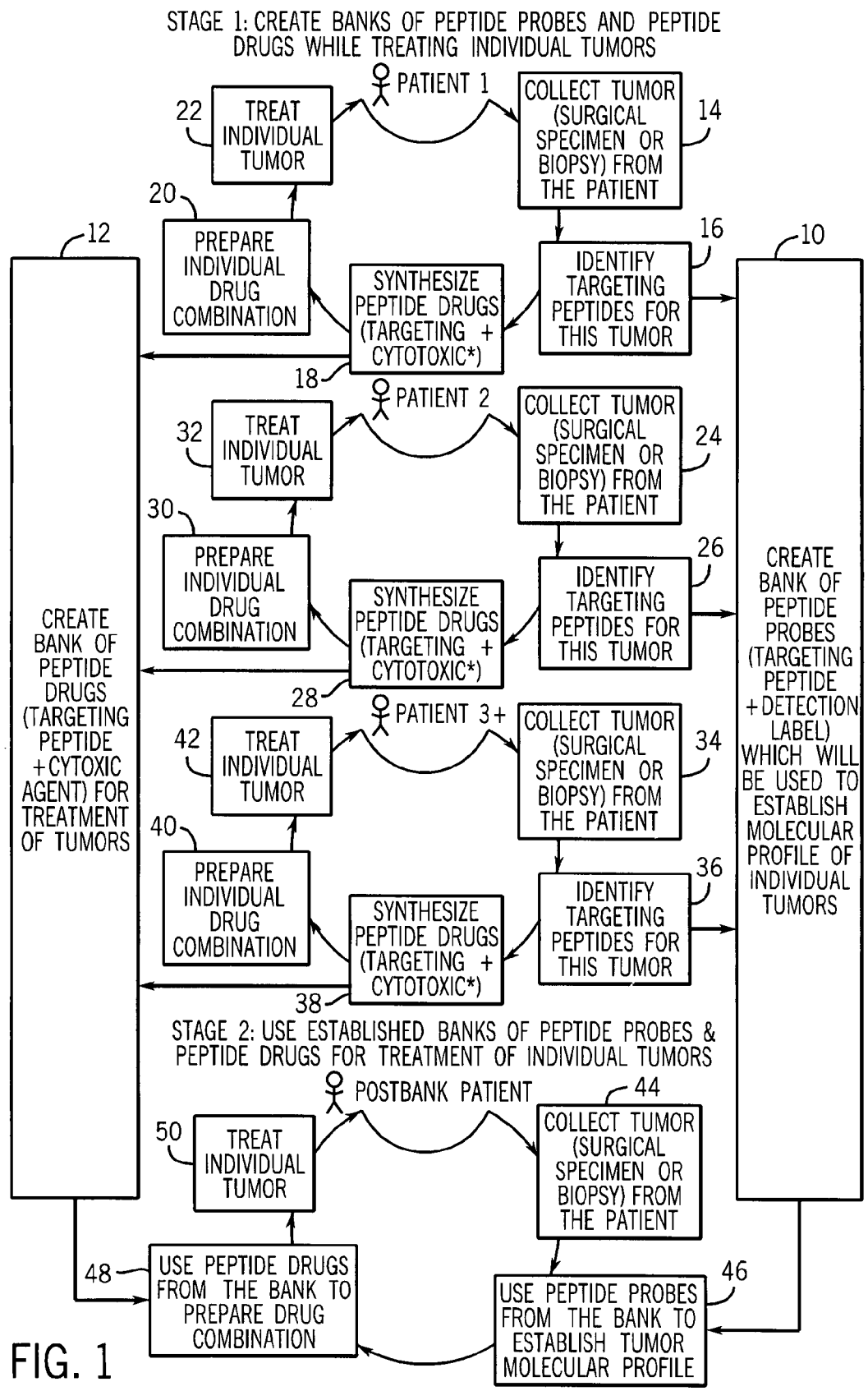
FIG. 1 is a schematic representation of a novel diagnostic strategy in anti-cancer drug design and treatment of individual tumors in accordance with the present invention.

Referring now to the drawings, FIG. 1 schematically illustrates both the diagnostic technique as well as the individualized anti-cancer treatment strategy disclosed herein. As illustrated, the strategy involves two stages. The first stage is the creation of a bank of peptide probes, sometimes referred to herein as target probes, and a bank of peptide drugs, sometimes referred to herein as target drugs, while treating individual tumors of numerous patients. The second stage involves using the established banks of peptides probes and peptide drugs for treatment of individual tumors of third party patients by not only determining the appropriate targeting drug or drugs to be utilized against that tumor, but also to administer the targeting drug or drugs to the patient.

Stage 1 involves the creation of a bank of peptide probes and a bank of peptide drugs. The bank of peptide probes is designated by the number 10, and the bank of peptide drugs is designated by the number 12. Each peptide probe comprises a targeting peptide linked to a detection label such as a fluorescent agent, a radioisotope, an enzyme or a metal particle. Each bank of peptide drug comprises a targeting peptide linked to a cytotoxic agent. That cytotoxic agent may be a cytotoxic peptide such as a lytic peptide, a radioisotope or any other cytotoxic agent that can be linked to the targeting peptide. The bank 10 of peptide probes is created from the treatment of individual tumors of numerous patients over time. For example, a sample of a first patient's cancer cells or tumor may be obtained or collected via a surgical specimen, a biopsy specimen, a blood specimen, or the like which is represented by the number 14. Thereafter, the cancerous cells are mixed with phage display library, bound phage clones are selected, and one or more targeting probes are identified that bind with the cancer cells. This step is identified as number 16 in FIG. 1 with respect to the first patient. A sample of each targeting probe is also placed into bank 10. Then, a peptide drug comprised of the same targeting peptide each linked to a cytotoxic agent is synthesized which is represented by the number 18. Finally, the one or more peptide drug, comprised of one or more targeting peptide each linked to a cytotoxic agent, is combined into a "cocktail" to be administered to the first patient. This step is illustrated by the number 20 in FIG. 1. A sample of each peptide drug is also placed into bank 12. Finally, the individual drug combination or cocktail of peptide drugs may be administered to the first patient to treat the individual tumor, which is designated by the number 22 in FIG. 1.

The above steps are repeated for any number of patients until a large enough bank 10 of peptide probes and bank 12 of peptide drugs is collected. Thus, steps 14-22 are repeated for a second patient, identified as steps 24-32, respectively in FIG. 1, as well as for a third patient, identified as steps 34-42, respectively in FIG. 1. Obviously, these steps are then repeated for any number of patients until an adequate number of peptide probes are collected in bank 10 and peptide drugs are collected in bank 12.

Once an adequate number of peptide probes are collected in bank 10 and peptide drugs are collected in bank 12, stage two of the present strategy can proceed. Stage two uses the established peptide probes in bank 10 and the peptide drugs in bank 12 for diagnosing and treating individual tumors of future patients, referred to in FIG. 1 as post-bank patients. Again, a sample of the post-bank patient's tumor is collected via any known technique, represented by number 44 in FIG. 1. This sample is prepared in any conventional manner to be mixed with targeting probes obtained from bank 10. After a sufficient incubation period, those targeting probes that bind to the cancer cells are identified, which step is designated as 46 in FIG. 1. Thereafter, the targeting peptide of the targeting probe identified to bind with the post-bank patient's cancer cells, is correlated to bank 12 of peptide drugs, each peptide drug having the same targeting peptide identified as binding to the cancer cells. An appropriate drug combination or cocktail of peptide drugs is then prepared, represented by the number 48 in FIG. 1. Thereafter, when used as a diagnostic technique, the drug combination is exposed to the cancer cells to induce a cytotoxic effect and the cytotoxic effect is quantified to determine efficacy, or when used as an anti-cancer treatment, the drug combination is administered to a patient to expose the cancerous tumor to the drug combination and induce a cytotoxic effect thereto. This latter treatment step is identified by the number 50 in FIG. 1.

Figures 4A, 4B:
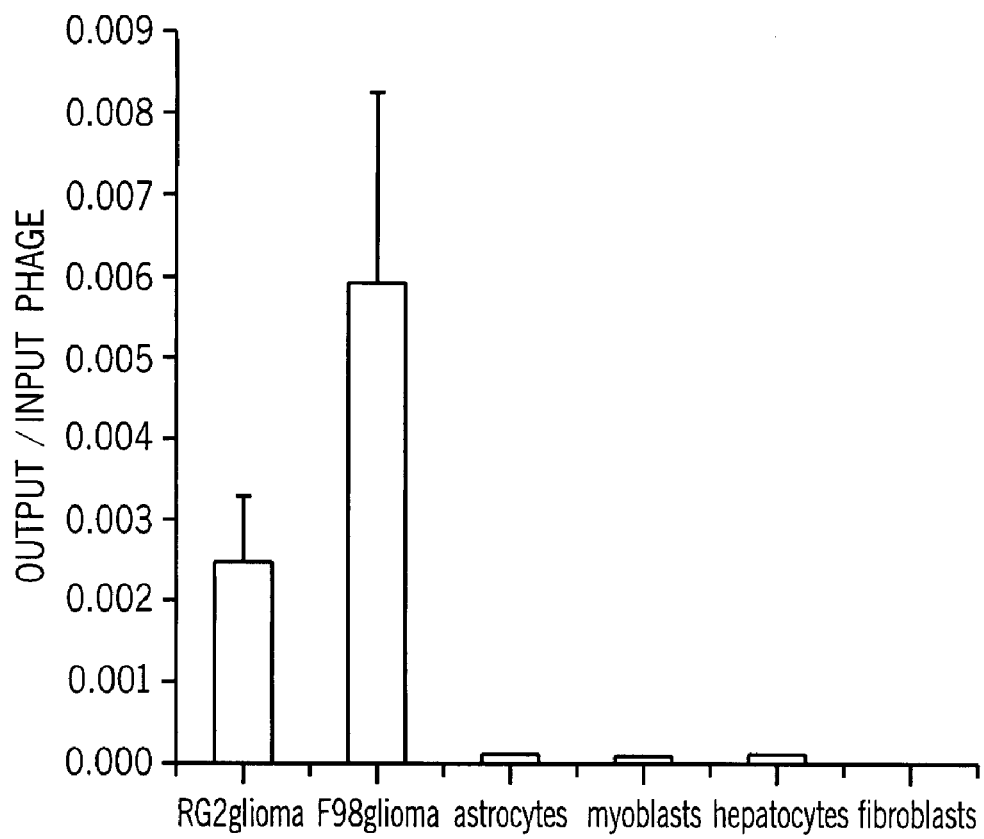
FIG. 4(*a*) illustrates the peptide sequences of three families of targeting peptides that bound to glioma cancer cells in accordance with the selection procedure of FIG. 3.
Figure 5A:
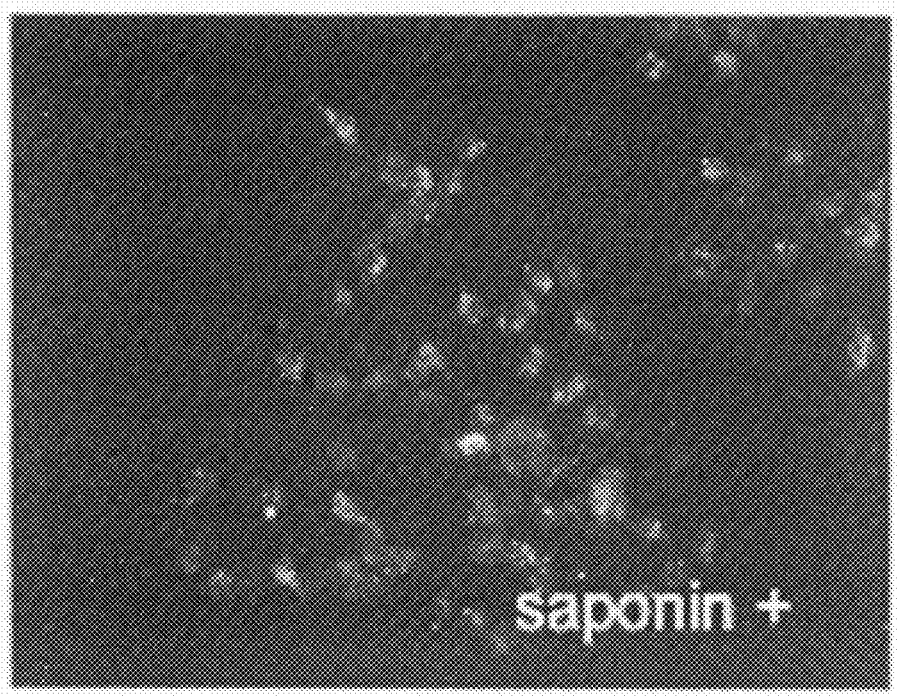
FIG. 5(*a*) is a pair of fluorescent microscope images of DSTKSGNM phage probes bound to glioma cancer cells treated with saponin (saponin+) to permeabilize cell membranes versus untreated cancer cells (saponin−)
Figure 5A:
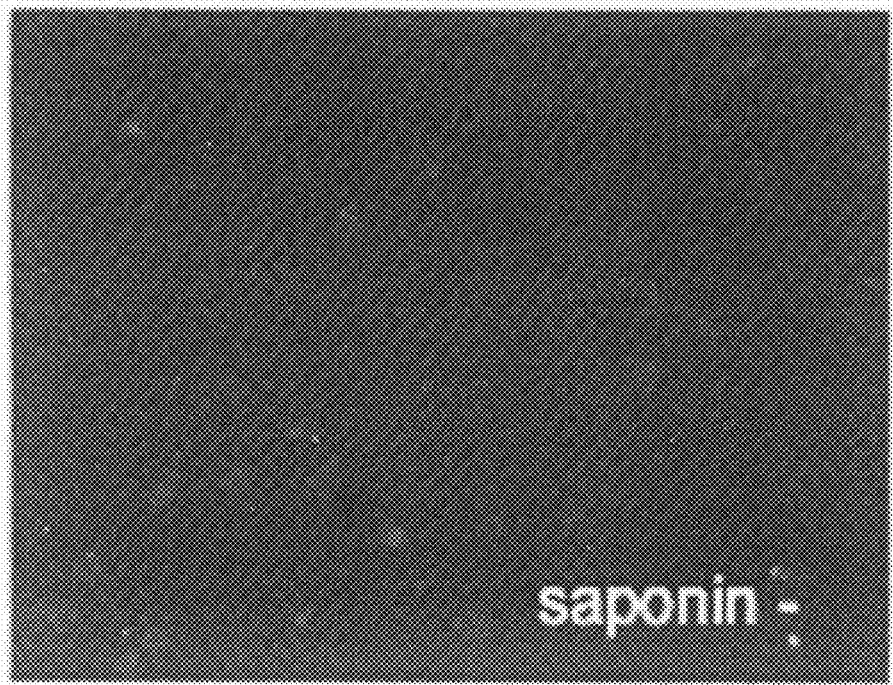

The following is a brief explanation of the phage display technique (FIGS. 2 and 3) used herein to identify the targeting probes that profile cancer tumors at the molecular level, and an example that demonstrates the feasibility of the molecular targeting approach (FIGS. 4 and 5). The goal of this strategy is to match anti-cancer peptide drugs to the molecular profiles of individual tumors. It includes the development of two banks, both of which will use the same set of targeting peptides. Targeting peptides are identified using biopsies or other tissue materials from multiple cancer patients and placed into two banks. For a bank of probes, targeting peptides are linked to a label (fluorescence, radioisotope, etc.). For a bank of drugs, targeting peptides are linked to a cytotoxic peptide to form a "targeting drug". Peptide probes are used to establish molecular profiles of individual tumors. Based on these molecular profiles, a patient-specific combination of targeting drugs from the bank of peptide drugs is prepared and the patient is treated. Any currently used cytotoxic agent that can be linked to targeting peptides may be used in place of cytotoxic peptides.

Targeting molecules, by definition, have high affinity to specific cell surface markers and, therefore, they can recognize and bind to specific cell types. For example, targeting molecules identified for cancer cells can discriminate between cancer and normal cells and, therefore, they are able to deliver cytotoxic agents directly to the target tumor cell, sparing normal tissues. Thus, the present technique for the identification of the targeting peptides comprises the selection of such peptides from random phage display peptide libraries.

Figure 2:
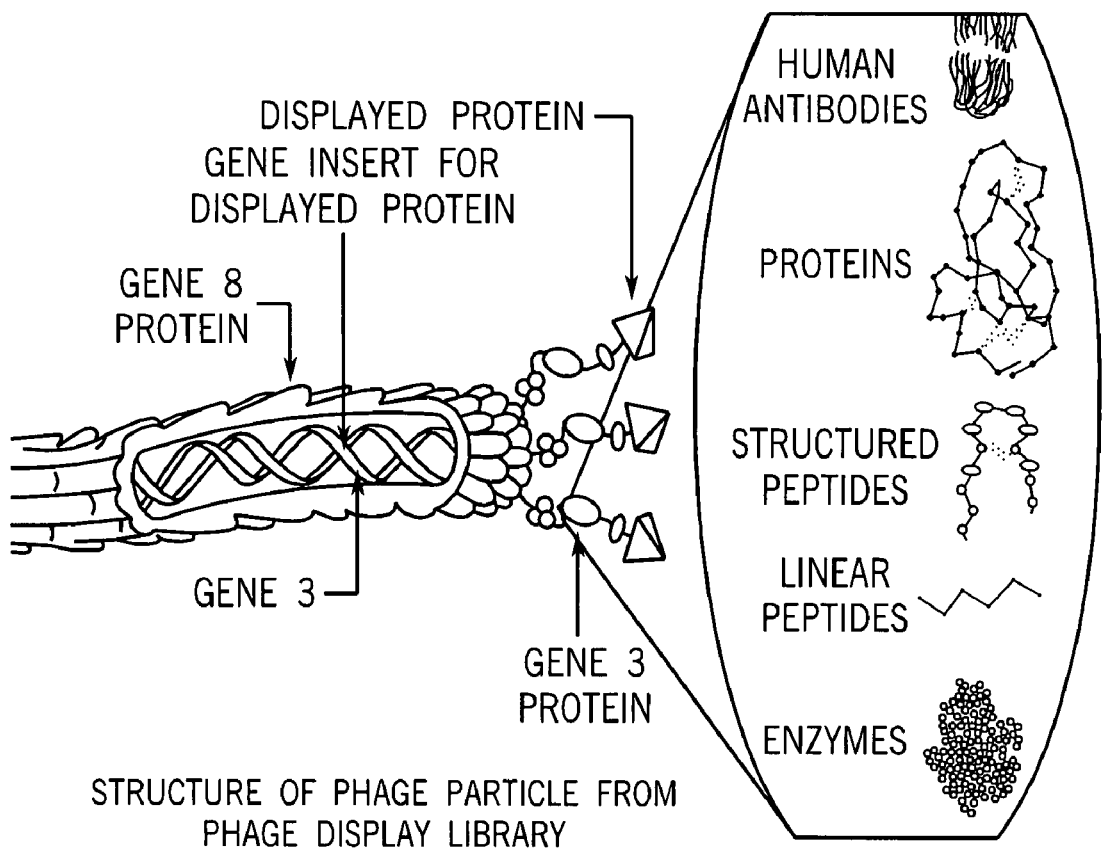
FIG. 2 is a schematic illustration of the phage display technique utilized to identify targeting peptides that bind to cancer tumors. The illustration is reproduced from Dyax Corporation of Cambridge, Mass.

FIG. 2 is a schematic illustration of a filamentous phage particle. Phage display libraries are constructed by the insertion of a DNA fragment, fixed in length but with random codons, in a phage surface protein gene. In the case shown in FIG. 2, this is gene III that encodes minor coat protein. The insertion of random oligonucleotide sequences results in a fusion protein that is expressed on the phage surface.

Figure 3:
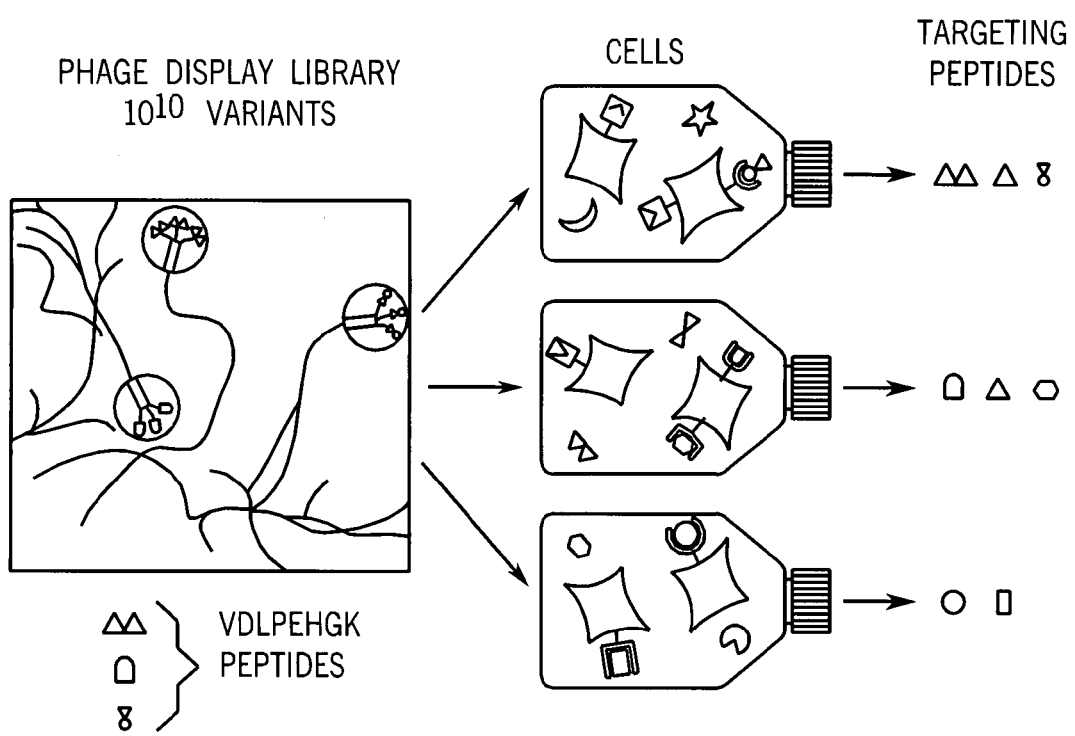
FIG. 3 is a schematic representation of the selection process for identifying targeting peptides from phage display libraries.

There are about $10^{10}$ different phage clones per library. Thus, a phage display library is a mixture of phage clones, each with a different peptide expressed on its surface. In FIG. 3, different peptides are shown in different shapes. Any known simple selection procedure may be used to pull out from the library those phage clones which recognize and bind to the desired cell type. This is a key-lock situation. If a peptide fits the receptor on the surface of the cell, it binds to that receptor. Phage DNA of such bound clones is sequenced and translated into its peptide sequence. Thus, for each cell type, those peptides which are specific for binding only to these cells can be identified.

Proteomic profiling as a method of developing personalized drugs to treat cancer is very desirable. In other words, if patients are to be treated with molecular means, then they need to be diagnosed at a molecular level. This requires molecular profiling. Genomic profiling of a disease is a good tool, but after post-translational modifications, protein targets may change and differ greatly from those identified via genomic profiling. Therefore, it is desirable to provide proteomic profiling which can be accomplished with peptides identified via phage display in accordance with the present inventive methods.

EXAMPLES

FIG. 4(*a*) shows three peptide families selected for rat brain tumor cells (glioma) (published in Samoylova et al, "Phage Probes for Malignant Glial Cells," Molecular Cancer Therapeutics, pages 1129-1137 (2003)). The first family of peptides appeared to target a marker that is common for glioma cells, normal brain cells, and cells of non-brain origin. The second group or family of peptides contains peptides with pronounced glioma-selective properties (see FIG. 4(*b*)). Binding of phage expressing peptide with this consensus sequence to two gliomas was several magnitudes higher than binding to normal cells (see paper mentioned above). Because this peptide sequence was very selective for cancer cells, this peptide was used as the peptide later on as a targeting moiety to create an anti-cancer cytotoxic agent (see FIGS. 5(*a*) and (*b*)). The third family demonstrated 63-fold glioma selectivity when compared to normal brain cells, astrocytes.

Using glioma-selective sequences from the second family shown in FIG. 4 (and in FIG. 5(*a*)), a fusion molecule containing the same identical cell-targeting peptide coupled to a cell-killing peptide was designed and synthesized. Glioma cells (malignant cells originating from astrocytes) and normal astrocytes were treated with increasing concentrations (10 or 100 uM) of cytotoxic peptide alone, or cytotoxic peptide linked to the targeting peptide, i.e. the peptide drug, and cytotoxicity was evaluated by MTT assay (this assay measures cell viability). None of the peptides, with or without targeting, demonstrated any effect on the normal astrocytes. However, the fusion molecule containing targeting and cytotoxic peptides, i.e. the peptide drug, resulted in a clear cytotoxic effect on glioma cells while non-targeted cytotoxic peptide alone had no effect on the tumor cells.

As described earlier herein, FIG. 2 schematically illustrates the phage display technique used in the present method.

FIG. 3 is a schematic representation of the phage display library selection process. A phage library is added to a flask with cultured target cells and incubated for a fixed time. During the incubation, phage that display peptides specific to the cell-surface molecules bind to the target. Unbound phage are then washed away. Bound phage are recovered from the cells, amplified in bacteria, purified, and added to target cells for each following round of selection. After three to four rounds, individual phage clones are sequenced to determine peptide sequences.

FIG. 4(a) illustrates peptide sequences that represent three families of RG2 glioma-selected phage. To obtain phage probes for molecular profiling of glioma cells, several independent phage display selection experiments were preformed in this study. In all experiments, a single landscape phage display library was used, while the conditions were modified. FIG. 4(b) illustrates the selectivity of glioma-specific DSTKSGNM (SEQ ID NO:3) phage clone for RG2 glioma cells and control cells. RG2 glioma and control cells were incubated with DSTKSGNM (SEQ ID NO:3) phage clone. Phage titers were determined by infection of bacteria and plotted as output to input ratios (Y axis) against different cell types, including RG2 and F98 gliomas, astrocytes, myoblasts, hepatocytes and fibroblasts (X axis). For more details, see the Samoylova et al article in Molecular Cancer Therapeutics, supra.

FIG. 5(a) illustrates the detection of internalized phage particles by immunofluorescence microscopy. RG2 glioma cells were grown on chamber slides and incubated with DSTKSGNM (SEQ ID NO:3) phage. In cells treated with saponin (saponin+) to permeabilize cell membranes, both internalized and extracellular bound phage particles were accessible for staining. Without saponin treatment (saponin−), FIG. 5(a) illustrates that only extracellular phage were available for detection. These slides were then processed for immunofluorescence microscopy with antibody against filed phage, followed by a fluorescein-conjugated secondary antibody to visualize phage particles. The comparison between saponin-treated and untreated cells indicated that glioma-specific DSTKSGNM (SEQ ID NO:3) phage were internalized by rat glioma RG2 cells.

Figure 5B:
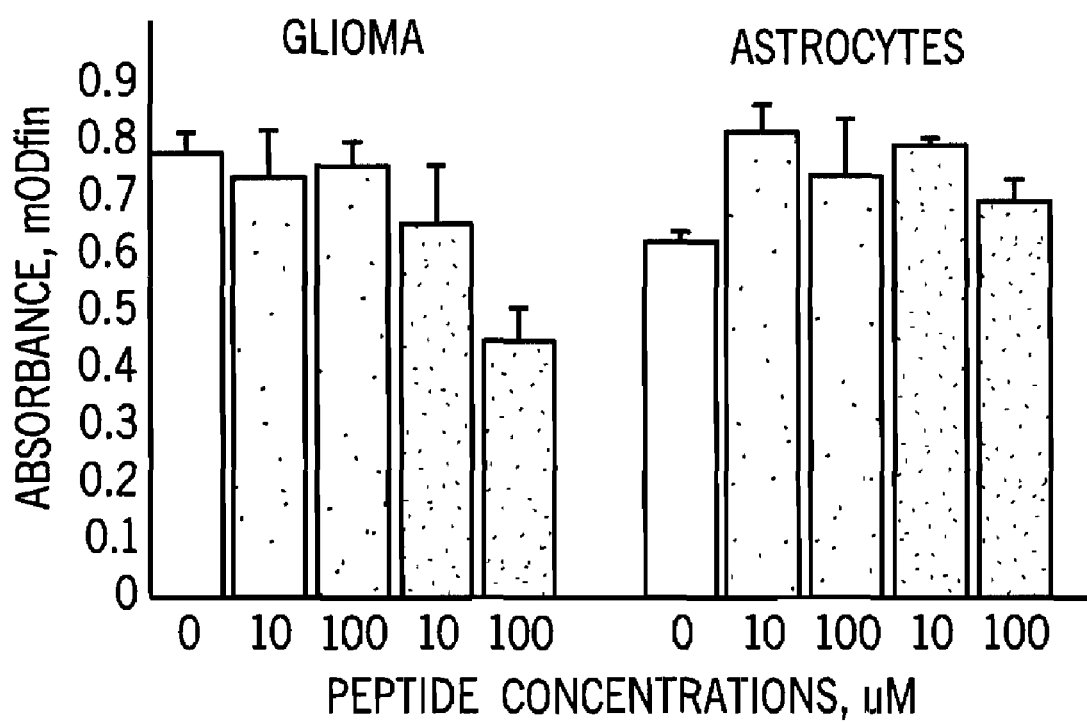

Referring to FIG. 5(b), the glioma are tumor cells and the astrocytes are normal cells. The unshaded bars in both cell illustrations represent absorbance with no treatment, while the gray shaded bars in both illustrations represent absorbance with control peptides. The sequence for the control peptide illustrations is d(KLAKLAK)$_2$(SEQ ID NO:4). The black shaded bars in both cell illustrations represent absorbance with targeting peptides linked to the control peptides. The sequence for the targeting peptide illustrations is DSTK-GG-d(KLAKLAK)$_2$(SEQ ID NO:5, wherein "GG" is the linker and "DSTK" (SEQ ID NO:6) is the targeting peptide.

FIG. 5(b) further illustrates the cytotoxic effect of d(KLAKLAK)$_2$(SEQ ID NO:4) and DSTK-GG-d(KLAKLAK)$_2$(SEQ ID NO:5) peptides on the glioma cells and the normal astrocytes. RG2 glioma cells and normal rat astrocytes were plated in quadruplicate in 96-well plates for 24 hours. Increasing concentrations (10 or 100 uM) of cytotoxic peptide alone, d(KLAKLAK)$_2$(SEQ ID NO:4), or cytotoxic peptide linked to targeting peptide, DSTK-GG-d(KLAKLAK)$_2$(SEQ ID NO:5), were added to the cells for 48 hours incubation. Cytotoxicity of therapeutic peptides were evaluated by MTT assay.

We claim:

1. A method of killing glioma cells in vitro comprising contacting the glioma cells with an effective concentration of a fusion protein;

the fusion protein comprising a targeting peptide fused at a C-terminus via a linking peptide to a cytotoxic peptide and having a formula:

(targeting peptide)–(linking peptide)–(cytotoxic peptide)

wherein the targeting peptide comprises an amino acid sequence DSTK (SEQ ID NO:6), the linking peptide comprises an amino acid sequence GG, and the cytotoxic peptide comprises an amino acid sequence d(KLAKLAK)$_2$ (SEQ ID NO:4); and wherein the fusion protein binds the glioma cells, the fusion protein is internalized by the glioma cells, and the fusion protein kills the glioma cells.

2. The method of claim 1, wherein the targeting peptide consists of an amino acid sequence DSTK (SEQ ID NO:6).

3. The method of claim 1, wherein the linking peptide consists of an amino acid sequence GG.

4. The method of claim 1, wherein the cytotoxic peptide consists of an amino acid sequence d(KLAKLAK)$_2$ (SEQ ID NO:4).

5. The method of claim 1, wherein the fusion protein comprises an amino acid sequence DSTK-GG-d(KLAKLAK)$_2$ (SEQ ID NO:5).

6. The method of claim 1, wherein the fusion protein consists of an amino acid sequence DSTK-GG-d(KLAKLAK)$_2$ (SEQ ID NO:5).

7. The method of claim 1, wherein the effective concentration is 10 μM.

8. The method of claim 1, wherein the effective concentration is 100 μM.

* * * * *